United States Patent [19]

Kluger et al.

[11] Patent Number: 4,761,502

[45] Date of Patent: Aug. 2, 1988

[54] POLYALKYLENEOXYTRIFLUOROME-THYLANILINE COMPOUNDS

[75] Inventors: Edward W. Kluger, Pauline; Patrick D. Moore, Spartanburg; Joe T. Burchette, Mayo, all of S.C.

[73] Assignee: Milliken Research Corporation, Spartanburg, S.C.

[21] Appl. No.: 904,459

[22] Filed: Sep. 8, 1986

[51] Int. Cl.[4] ........................ C07C 87/28; C07C 87/60
[52] U.S. Cl. ................................ 564/442; 260/404; 260/404.5; 560/250; 560/251; 560/252; 558/394
[58] Field of Search .............................. 564/442, 443

[56] References Cited

U.S. PATENT DOCUMENTS

| 2,876,263 | 3/1959 | Mark | 564/443 |
| 3,403,131 | 9/1968 | Garnish | 564/442 |
| 4,658,064 | 4/1987 | Moore et al. | 564/443 |

FOREIGN PATENT DOCUMENTS 3201112  7/1983  Fed. Rep. of Germany ...... 564/442

OTHER PUBLICATIONS

Freifelder et al, "Chem. Abstracts", 55:23390h (1961).
Freifelder et al, J. Org. Chem. 26, 1477-80 (1961).
Ash et al, "Chem. Abstracts", 60:12028c (1964).

Primary Examiner—J. E. Evans
Attorney, Agent, or Firm—Terry T. Moyer; H. William Petry

[57] ABSTRACT

Polyalkyleneoxytrifluoromethylaniline compounds are provided of the formula:

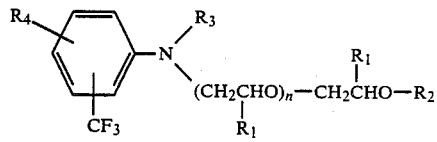

wherein $R_1$ is independently selected from H, a lower alkyl group containing from 1 to about 10 carbon atoms, $CH_2Cl$, $CH_2Br$, $CH_2OH$, phenyl or

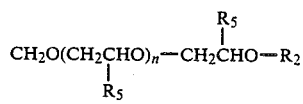

where $R_5$ is H or a lower alkyl group containing from 1 to about 9 carbon atoms; $R_2$ is selected from H, a lower alkyl group containing from 1 to about 9 carbon atoms, alkylaryl containing from 7 to about 11 carbon atoms, cyanoalkyl, or acyl; $R_3$ is selected from a lower alkyl group containing from 1 to about 9 carbon atoms, cyanoalkyl, acetoxyalkyl or

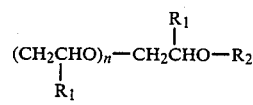

wherein $R_1$ and $R_2$ are as given above; $R_4$ is H, $CF_3$, a lower alkyl group containing from 1 to about 9 carbon atoms, Cl or Br and n is 0 or an integer from 1 to about 125.

9 Claims, No Drawings

POLYALKYLENEOXYTRIFLUOROMETHYLANILINE COMPOUNDS

The present invention relates to novel polyalkyleneoxytrifluoromethylaniline compounds.

The compounds of the present invention fall into the broad category of chemical intermediates. Such chemical intermediate compounds, in general, may be said to have broad application in the preparation of other chemical compounds. The particular polyalkyleneoxytrifluoromethylaniline compounds of the present invention have utility as intermediates in the preparation of polymeric, reactive dyes having increased resistance to tin reduction in polyurethane systems. It is believed that these intermediates may also be useful in the preparation of polymeric colorants having improved heat stability and, in general, brighter colors.

The compounds of the present invention may be most appropriately described by reference to the following formula:

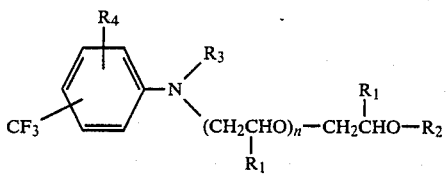  I.

wherein $R_1$ is independently selected from H, a lower alkyl group containing from 1 to about 10 carbon atoms, $CH_2Cl$, $CH_2Br$, $CH_2OH$, phenyl or

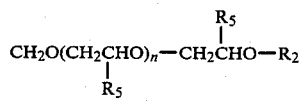

where $R_5$ is H or a lower alkyl group containing from 1 to about 9 carbon atoms; $R_2$ is selected from H, a lower alkyl group containing from 1 to about 9 carbon atoms, alkylaryl containing from about 7 to about 11 carbon atoms, cyanoalkyl, or acyl; $R_3$ is selected from a lower alkyl group containing from 1 to about 9 carbon atoms, cyanoalkyl, acetoxyalkyl or

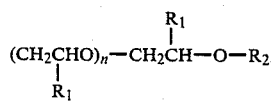

wherein $R_1$ and $R_2$ are as given above; $R_4$ is H, $CF_3$, a lower alkyl group containing from 1 to about 9 carbon atoms, Cl or Br and n is 0 or an integer from 1 to about 125.

According to a preferred embodiment, the trifluoromethyl group may be provided on the meta position of the aromatic portion of the molecule.

The present invention also relates to a method for preparing polyalkyleneoxides containing trifluoromethylanilines as set forth in formula I above.

An embodiment of the present invention involves a process which comprises the reaction of a trifluoromethylaniline compound of the formula:

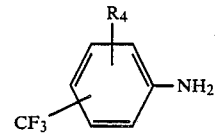

in the presence or absence of acid catalyst with an alkylene oxide of the formula

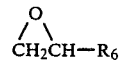

wherein $R_6$ is selected from H, $CH_2OH$, $CH_2Cl$, or a lower alkyl group having from 1 to about 9 carbon atoms and $R_1$, $R_2$, $R_3$, and $R_4$ are as set forth before.

According to an alternative embodiment, the trifluoromethylaniline as set forth in formula I above may be hydroxyalkylated by the reaction of an alkyl halide of the formula:

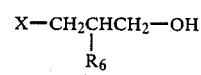

in the presence of a base wherein X is Cl, Br or I and $R_6$ has the value given above.

Yet another embodiment of the present invention involves the generation of the corresponding polyalkyoxyhydroxytrifluoromethylanilines of the formula:

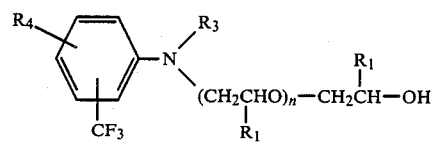  II.

wherein $R_1$, $R_3$, and $R_4$, and n have the values given above, by the reaction of the trifluoromethylaniline with a base catalyst.

Another embodiment of the invention involves the end termination of the hydroxyl groups by an alkylating agent to give derivatives of the formula:

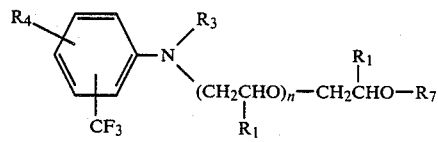  III.

wherein $R_7$ is lower alkyl, cyanoalkyl, or

wherein $R_8$ is lower alkyl or aryl.

A preferred embodiment of this invention will be described with particular reference to the trifluoromethylaniline employed. This invention is not to be limited, however, to the use of trifluoromethyl aniline, per se, in the non-basic hydroxyalkylation reaction. Other suitable trifluoromethylanilines may be employed including 2-amino-5-chlorobenzotrifluoride, 3-amino-4-chlorobenzotrifluoride, 3-amino-6-chlorobenzotrifluoride and 3,5-bis-trifluoromethylaniline. As a further embodiment of the non-basic hydroxyalkylation of the m-trifluoromethylaniline, ethylene oxide is employed in the hydroxyalkylation. This invention is not limited, however, to the use of ethylene oxide, per se, in the non-basic hydroxyalkylation step. Other suitable hydroxyalkylation agents include, for example, propylene oxide, butylene oxide, epichlorohydrin, cyclohexene oxide, glycidyl and mixtures of two or more of such compounds.

The hydroxyalkylation may be accomplished by the reaction of the alkylene oxide at about 90° C. to about 150° C. The alkylene oxide is added in the presence of an inert gas such as nitrogen until two or more equivalents of alkylene oxide have been absorbed. An inert solvent can also be used if so desired that boils at about 100° C. to about 150° C. For example toluene, xylenes, nitrobenzene, dioxane are just a few inert solvents that may be used. Alternatively, an acid catalyst can be employed to effect the hydroxyalkylation. For example formic acid, and acetic acid are just a few examples of such inert acids that may be used.

Generally, acid-catalyzed hydroxyalkylation is performed at a lower temperature to avoid the formation of by-products. Temperatures from about 60° C. to about 120° C. can be employed depending on the trifluoromethylanilines to be hydroxyalkylated. The amount of acid catalyst may also vary widely. Generally from about 0.5% to 10% maybe employed.

Another preferred embodiment of this invention will be described with particular reference to the use of ethylene oxide in the base-catalyzed polyoxyalkylation step. This invention is not limited, however, to the use of ethylene oxide, and other suitable alkylene oxides or mixtures thereof may be used as set forth above.

The corresponding polyoxyalkylated intermediates may be prepared by further reaction of the dihydroxyethyltrifluoromethylaniline by adding an appropriate basic catalyst such as potassium hydroxide to the reaction mixture, and then adding further quantities of the desired alkylene oxide or mixtures thereof. Other basic catalysts can also be used such as lithium hydroxide, calcium hydroxide, and barium hydroxide, just to name a few. The amount of basic catalyst can vary but is usually in the range of from about 0.2% to about 2% by weight. The reaction temperature may also vary but may generally be in the range from about 100° C. to about 150° C. and preferably from about 130° C. to about 150° C.

Yet another embodiment of this invention relates to the end termination alkylation step. This step is described with particular reference to acrylonitrile as the alkylating agent, although it is not to be limited to use of acrylonitrile, per se. Other suitable alkylating agents are crotonitrile, and/or methacrylonitrile just to name a few. In addition, different classes of alkylating agents may be employed as end termination agents. These include anhydrides, acid chlorides, dialkylsulfates, trialkylphosphates and alkyl halides just to name a few.

In accordance with these preferred embodiments, bis-2-cyanoethyl-m-trifluoromethylaniline having about ten ethylene oxide groups (hereinafter 1OEO) may be produced by the polyoxyalkylation of m-trifluoromethylaniline with two moles of ethylene oxide in the non-basic alkylation step in the presence or absence of a solvent. The corresponding m-trifluoromethylphenyldiethanolamine may be then converted into the m-trifluoromethylaniline 1OEO intermediate in the presence of potassium hydroxide catalyst. Finally, the novel bis-2-cyanoethyl-m-trifluoromethylaniline 1OEO intermediate may be obtained in high yield by the cyanoethylation of the 1OEO-metal-trifluoromethylaniline intermediate in the end termination step. The corresponding dinitrile is produced in high yield by the reaction of lithium hydroxide catalyst and acrylonitrile as shown in the scheme below:

SCHEME

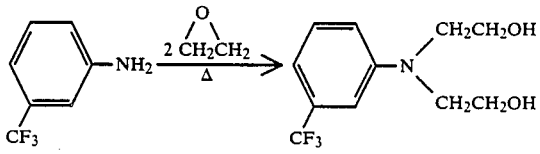

NON BASIC HYDROXYALKYLATION STEP

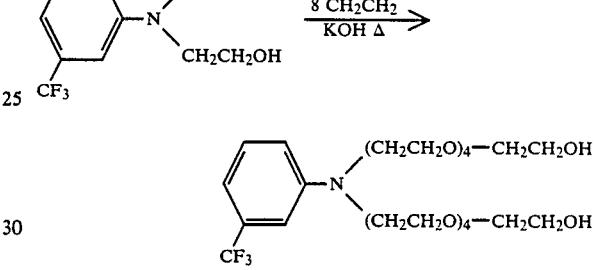

BASE CATALYZED POLYOXYALKYLATION STEP

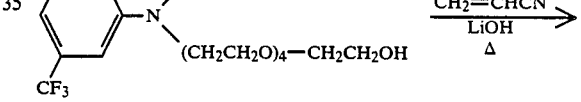

END TERMINATION STEP

The invention may be further understood by reference to the following examples which are not to be construed as limiting the scope of the invention. Unless otherwise indicated all parts and percentages are by weight.

EXAMPLE 1

In a two liter autoclave was charged 900 gms (5.59 moles) of 3-aminobenzotrifluoride. The reactor was purged three times with nitrogen and then heated to 250° F. under 5 psi nitrogen pressure. Next 500 gms (11.4 moles) ethylene oxide was added to the reaction over three hours. After three hours a sample was pulled and the hydroxyl number was determined to be 447.9 (theory-450.6). The sample was also analyzed by GC-Mass spectra and found to contain no starting material. The product mixture yielded 1373 gms of crude product containing about 12.7% monohydroxyethyl-3-aminobenzotrifluoride and 89.9% of the dihydroxyethyl-3-aminobenzotrifluoride. This amounts to a yield of 88.7% for the dihydroxyethyl-3-aminobenzotrifluoride.

EXAMPLE 2

In a two liter autoclave was charged 1000 gms (6.21 moles) of 3-aminobenzotrifluoride. The reactor was purged three times with nitrogen and then heated to 250° F. under 5 psi nitrogen pressure. Next 500 gms (12.5 moles) of ethylene oxide was added to the reaction mixture over six hours. After six hours a sample was pulled and the hydroxyl number was determined to be 447.9 (theory-450.6). The sample was also analyzed by GC-mass-spectra and found to contain no starting material. The product mixture yielded 1511 gms of crude product containing about 78.2% of dihydroxyethyl-3-aminobenzotrifluoride and 21.8% of the triethoxylated derivative. This amounts it a yield of 76.4% for the dihydroxyethyl-3-aminobenzotrifluoride. A portion of this crude product was taken and recrystalized four times from ethanol-water to give a white solid that melted sharply at 83° C. to 85° C. A GC mass spectrum of this material showed only the pure dihydroxyethyl-3-aminobenzotrifluoride.

EXAMPLE 3

In a two liter autoclave was charged 500 gms (3.10 moles) of 3-aminobenzotrifluoride, and 2.5 gms of formic acid catalyst. The reactor was purged three times with nitrogen and heated to 200° F. under 5 psi nitrogen pressure. Next, 275 gms (6.25 moles) of ethylene oxide was added to the reaction over five hours. After six hours a sample was pulled and was analyzed by GC mass spectra and found to contain no starting material. The product mixture yielded 756 gms of crude product containing about 78.2% of the dihydroxyethyl-3-aminobenzotrifluoride and 21.8% of the trihydroxyethylated product. This amounts to a yield of 78.2% for the dihydroxyethyl-3-aminobenzotrifluoride.

EXAMPLE 4

In a two liter autoclave was charged 500 gms (3.10 moles) of 3-aminobenzotrifluoride, and 2.5 gms of formic acid catalyst. The reactor was purged three times with nitrogen and heated to 200° F. under 5 psi nitrogen pressure. Next 275 gms (6.25 moles) of ethylene oxide was added to the reaction over three hours. Afterward an additional 120 gms (2.7 moles) of ethylene oxide was added and the reaction mixture was heated for an additional five hours. After nine hours a sample was pulled and was analyzed by GC mass spectra and found to contain 17% of the dihydroxyethyl-3-aminobenzotrifluoride, 71.5% of the trihydroxyethylated product and 10.5% of the tetrahydroxyethylated product.

EXAMPLE 5

In a two liter autoclave was charged 500 gms (2.56 moles) of 3-amino-4-chlorobenzotrifluoride and 10 gms of acetic acid catalyst. The reactor was purged three times with nitrogen and then heated to 200° F. under 5 psi nitrogen pressure. Next, 225 gms (5.1 moles) of ethylene oxide was added to the reaction over 9 hours. A sample was then pulled and analyzed by GC mass spectra and found to contain dihydroxyethyl-3-amino-4-chlorobenzotrifluoride in addition to some monohydroxyethyl-3-amino-4-chlorobenzotrifluoride. The product reaction mixture amounted to 700 gms.

EXAMPLE 6

In a two liter autoclave was charged 200 gms (2.56 moles) of 2-amino-5-chlorobenzotrifluoride and 20 gms of acetic acid catalyst. The reaction was purged three times with nitrogen and then was heated to 150° F. and 5 psi nitrogen pressure. Next, 90 gms (2.05 moles) of ethylene oxide was added to the reaction over about 10 hours. At this time a sample was pulled and was analyzed by GC mass spectra. The reaction mixture was found to contain the dihydroxyethyl-2-amino-5-chlorobenzotrifluoride. The crude reaction product amounted to 290 gms.

EXAMPLE 7

In a two liter autoclave was charged 220 gms (0.96 moles) of 3,5-bis-trifluoromethylaniline and 25 gms of acetic acid. The reaction was purged three times with nitrogen and then heated to 250° F. under 5 psi nitrogen pressure. Next 100 gms (2.27 moles) of ethylene oxide was added to the reactor over 8 hours. At this time a sample was pulled and was analyzed by GC mass spectra. This reaction mixture was determined to contain about 70% of the dihydroxyethyl-bis-3,5-trifluoromethyaniline, 15% of the monohydroxyethyl-3,5-bis-trifluoromethylaniline and 15% of the trihydroxyethylated products. The crude reaction product amounted to 266 gms. This amounted to a yield of 58.6% for the dihydroxyethyl-3,5-bis-trifluoromethylaniline.

EXAMPLE 8

In a two liter three necked flask equipped with mechanical stirrer, refluxing condenser and thermometer was added 322.2 gms (2.0 moles) of 3-aminobenzotrifluoride, 500 ml of ethoxyethanol solvent and 442.0 gms (4 moles) 1-chloro-2,3-propanediol. While this mixture was cooling, 205 gms (2.36 moles) of sodium carbonate was added keeping the temperature below 35° C. The mixture was then heated to reflux for 24 hours. Afterwards, the crude reaction mixture was filtered from the salt by-product. The salt was then washed several times with chloroform and these washings were combined with the filtrate. The solvent and chloroform was then removed under low vacuum and high vacuum to give 450.5 gms of the crude bis-2,3-dihydroxypropyl-3-aminobenzotrifluoride as a viscous dark oil.

EXAMPLE 9

In a two liter autoclave was charged 306 gms (1.23 moles) of the dihydroxyethyl-3-aminobenzotriflouride prepared as described in Example 3 and 3 gms of potassium hydroxide catalyst. The reactor was purged three times to 60 psi with nitrogen. The reactor was then heated to 250° C. under 5 psi nitrogen pressure. Next, 860 gms (14.8 moles) of propylene oxide was added over an eight hour period. At this time the hydroxyl number was run for the reaction mixture and was found to be 121.6 (theory-118.7). Next, 435 gms (9.89 moles) of ethylene oxide was added over a seven hour period. Again the hydroxyl number was run for a sample of the reaction mixture and it was found to be 87.5 (theory 86.5). The reaction product was stripped under high vacuum to give 1600 gms of pale yellow product. This amounted to a 99.7% yield of the 3-aminobenzotrifluoride 2EO/12PO/8EO polymer of average molecular weight of 1297 gms/mole.

EXAMPLE 10

In a two liter autoclave was charged 300 gms (1.24 moles) of the dihydroxyethyl-3-aminobenzotrifluoride (prepared essentially as described in Example 2) and 2 gms of potassium hydroxide catalyst. The reactor was purged three times to 60 psi with nitrogen. The reactor was then heated to 270° F. under 5 psi nitrogen. Next, 955 gms (21.7 moles) of ethylene oxide was added over four hours. Then the hydroxyl number was run for the reaction mixture and was found to be 107.8 (theory-106.5). The reaction product was stripped under high vacuum to give 1249 gms of pale yellow product. This amounted to a 99.4% yield of the 3-aminobenzotrifluoride 2OEO polymer of average molecular weight of 1041 gms/mole.

EXAMPLES 11-19

Using the procedures of Examples 9 and 10, the other 3-aminobenzotrifluoride polyalkylene oxide polymers shown in Table 1 were also prepared:

TABLE 1

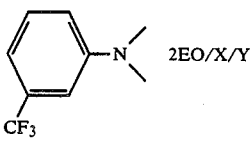

| EXAMPLE | X | Y | % YIELD | AVE. MOLECULAR WT. |
|---|---|---|---|---|
| 11 | 8 EO | 0 | 99.9 | 593 |
| 12 | 9 EO | 0 | 98.6 | 637 |
| 13 | 10 EO | 0 | 99.2 | 681 |
| 14 | 10 PO | 6 EO | 98.9 | 1085 |
| 15 | 15 PO | 5 EO | 99.4 | 1331 |
| 16 | 10 PO | 20 EO | 98.0 | 1701 |
| 17 | 12 PO | 6 EO | 97.0 | 1201 |
| 18 | 12 PO | 10 EO | 99.5 | 1377 |
| 19 | 13 PO | 0 | 98.5 | 995 |

EXAMPLE 20

In a two liter autoclave was charged 309 gms (1.0 moles) of the bis-2,3-dihydroxypropyl-3-aminobenzotrifluoride prepared as described in Example 8 and eight grams of potassium hydroxide catalyst. The reactor was purged three times to 60 psi with nitrogen. The reactor was then heated to 275° F. under 5 psi nitrogen pressure. Next, 440 gms (10 moles) of ethylene oxide was added over an eight hour period. At this time the hydroxyl number was run for the reaction mixture and was found to be 296.1 (theory-299.6). This reaction product was stripped under high vacuum to give 702.4 gms of orange yellow product. This amounted to a 93.7% yield of the bis-2,3-dihydroxypropyl-3-aminobenzotrifluoride 1OEO polymer of average molecular weight of 699 gms/mole.

EXAMPLES 21-24

Using the procedures of Example 19, the other bis-2,3-dihydroxypropyl-3-aminobenzotrifluoride polyalkylene oxide polymers shown in Table 2 were also prepared:

TABLE 2

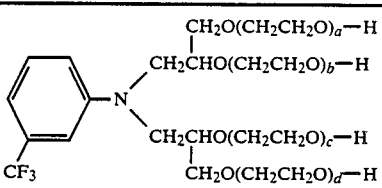

| EXAMPLE | X* | % YIELD | AVE. MOLECULAR WT. |
|---|---|---|---|
| 21 | 11 | 99.5 | 743 |
| 22 | 12 | 98.6 | 787 |
| 23 | 13 | 99.2 | 831 |
| 24 | 14 | 99.3 | 875 |

*X = a + b + c + d

EXAMPLE 25

In a 2000 cc beaker was added 500 gms (0.38 moles) of 3-aminobenzotrifluoride 2EO/15PO/5EO polymer, 239 gms (2.25 moles) of acetic anhydride and 3 drops of n-methylimidizole catalyst. After the initial reaction exotherm stopped, the reaction mixture was heated to 100° C. for 4 hours. Next, the dark yellow orange reaction mixture was stripped under low and then high vacuum (less 1 mm Hg) to give a yellow-orange oil. An IR spectrum indicated the absence of hydroxyl groups and the presence of the desired carbonyl and ester groups for this polymeric 3-aminobenzotrifluoride 2EO/15PO/5EO diacetate of average molecular weight of 1417 gms/mole.

EXAMPLE 26

In a two liter three necked flask equipped with an overhead stirrer, reflux condenser, nitrogen purge, dropping funnel and thermometer was charged 241 gms (2 moles) of dihydroxyethyl-3-aminobenzotrifluoride (premelted) as prepared in Example 2 along with 1.1 gms of anhydrous lithium hydroxide. The overhead stirrer was then adjusted to high speed and the flash was preheated to 50° C. with a water bath. Acrylonitrile was then added through the dropping funnel. Over the course of 1.2 hours a total of 159 gms (3 moles) acrylonitrile was added at a rate such that the reaction temperature did not exceed 74° C. The reaction flash was then heated to 66° C.-70° C. for 12 hours. The reaction contents were cooled to room temperature and made slightly acidic with 85% $H_3PO_4$. The reactor contents were then filtered. The crude filtered reaction product was stripped of all excess acrylonitrile under vacuum (15-30 mm Hg) at a temperature not exceeding 80° C. to give the pale yellow liquid, bis-2-cyanoethyl-3-trifluoromethylphenyldiethanolamine. An IR spectrum indicated the absence of the hydroxyl group and presence of the desired nitrile group.

EXAMPLE 27

In a two liter autoclave was charged 500 gms (3.10 moles) of 2-aminobenzotrifluoride, and 20 gms of acetic acid. The reactor was purged three times to 60 psi with nitrogen pressure. Next, 275 gms (6.25 moles) of ethylene oxide was added to the reactor over fifteen hours. At this time a sample was pulled and was analyzed by GC mass spectra. The reaction mixture was found to contain the dihydroxyethyl-2-amino-benzotrifluoride.

What is claimed is:
1. A compound of the formula:

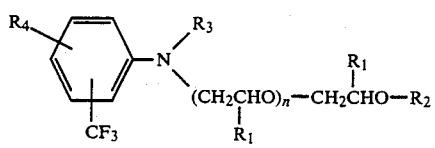

I.

wherein $R_1$ is independently selected from H, a lower alkyl group containing from 1 to about 10 carbon atoms, $CH_2Cl$, $CH_2Br$, $CH_2OH$, phenyl or

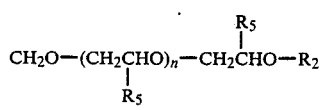

where $R_5$ is H or a lower alkyl group containing from 1 to about 9 carbon atoms; wherein $R_2$ is selected from H, a lower alkyl group containing from 1 to about 9 carbon atoms or, alkylaryl containing from about 7 to about 11 carbon atoms; $R_3$ is selected from a lower alkyl group containing from 1 to about 9 carbon atoms, or

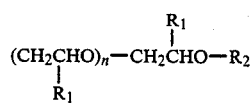

wherein $R_1$ and $R_2$ are as given above; $R_4$ is H, $CF_3$, lower alkyl group containing from 1 to about 9 carbon atoms, Cl or Br and n is an integer from 1 to about 125.

2. The compound of claim 1 wherein $R_2$ is hydrogen.

3. The compound of claim 1 where $R_2$ is a lower alkyl group containing from one to about nine carbon atoms.

4. A compound of the formula:

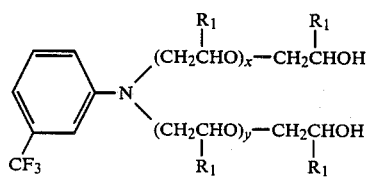

wherein $R_1$ equals H or methyl and $x+y=2$ to about 18 with the proviso that x and y must each be at least 1.

5. A compound of the formula:

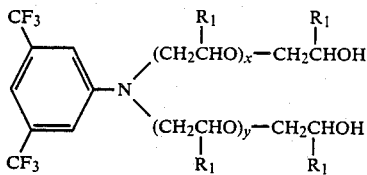

wherein $R_1$ equals H or methyl and $x+y=2$ to about 18 with the proviso that x and y must each be at least 1.

6. A compound of the formula:

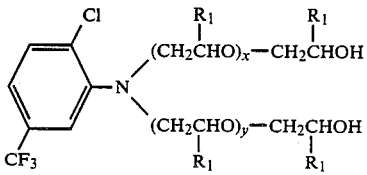

wherein $x+y=2$ to about 18 with the proviso that x and y must each be at least 1.

7. A compound of the formula

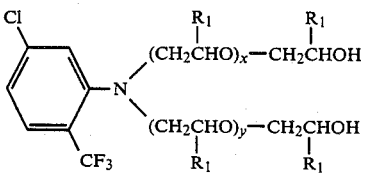

wherein $R_1$ equals H or methyl and $x+y=2$ to about 18 with the proviso that x and y must each be at least 1.

8. A compound of the formula

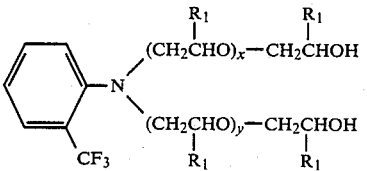

wherein $R_1$ equals H or methyl and $x+y=2$ to about 18 with the proviso that x and y must each be at least 1.

9. A compound of the formula:

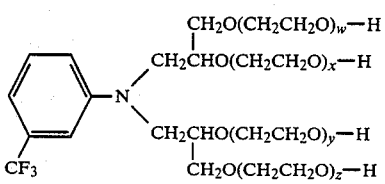

where $R_1$ equals H or methyl and $w+x+y+z$ equals 4 to about 18 with the proviso that w, x, y and z must each be at least 1.

* * * * *